US00PP37515P2

(12) United States Plant Patent
Berry

(10) Patent No.: US PP37,515 P2
(45) Date of Patent: Jul. 7, 2026

(54) ***LEUCOPHYLLUM* PLANT NAMED 'JBN SC2'**

(50) Latin Name: *Leucophyllum frutescens*
Varietal Denomination: JBN SC2

(71) Applicant: James Berry, Edgewood, TX (US)

(72) Inventor: James Berry, Edgewood, TX (US)

(73) Assignee: Capstone Plants Inc, Grand Saline, TX (US)

( * ) Notice: Subject to any disclaimer, the term of this patent is extended or adjusted under 35 U.S.C. 154(b) by 0 days.

(21) Appl. No.: 19/375,683

(22) Filed: Oct. 31, 2025

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

*Primary Examiner* — Kent L Bell

(57) ABSTRACT

A new and distinct cultivar of *Leucophyllum* plant named 'JBN SC2' is disclosed, characterized by silvery, canescent foliage, and large lavender flowers. Elliptic-shaped plants are compact and densely branched. Flowering occurs freely from summer to fall. The new variety is a *Leucophyllum*, typically produced as an outdoor ornamental plant.

2 Drawing Sheets

Latin name of the genus and species: *Leucophyllum frutescens.*

Cultivar denomination: 'JBN SC2'.

BACKGROUND OF THE INVENTION

The new cultivar is a product of a planned breeding program conducted by the inventor, to produce new *Leucophyllum frutescens* cultivars with silvery foliage, compact, tidy habits, and excellent garden performance. The crossing resulting in the new cultivar was made in summer of 2018 at a nursery in Terrell, Texas.

The seed and pollen parents are two unnamed, unpatented *Leucophyllum frutescens* varieties. The new cultivar was found and selected by the inventor in June of 2023 at the same nursery in Terrell, Texas. Asexual reproduction of the new cultivar 'JBN SC2' was first performed during June of 2023 in Grand Saline, Texas, by softwood cuttings. Through subsequent propagation, multiple additional generations have been reproduced, having shown that the unique features of this cultivar are stable and reproduced true to type.

SUMMARY OF THE INVENTION

The cultivar 'JBN SC2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JBN SC2'. These characteristics in combination distinguish 'JBN SC2' as a new and distinct *Leucophyllum* cultivar:

1. Compact, densely branched habit.
2. Upright, elliptic overall plant shape.
3. Silvery, canescent foliage.
4. Freely flowering habit with flowers appearing in bursts from summer to fall.
5. Large (2 cm diameter) lavender flowers.
6. Excellent garden performance.

PARENT COMPARISONS

Parent comparisons are unavailable.

COMMERCIAL COMPARISON

Plants of 'JBN SC2' can be compared to plants of the commercial cultivar *Leucophyllum frutescens* 'GREHJS', U.S. Plant Pat. No. 33,638. Plants of 'JBN SC2' are similar to plants of 'GREHJS' in most horticultural characteristics, however, plants of 'JBN SC2' differ in the following:

1. Internodes of the new cultivar are shorter than the internodes of this comparator.
2. Plants of the new cultivar are smaller at maturity than plants of this comparator.

BRIEF DESCRIPTION OF THE PHOTOGRAPHS

Figure 1:
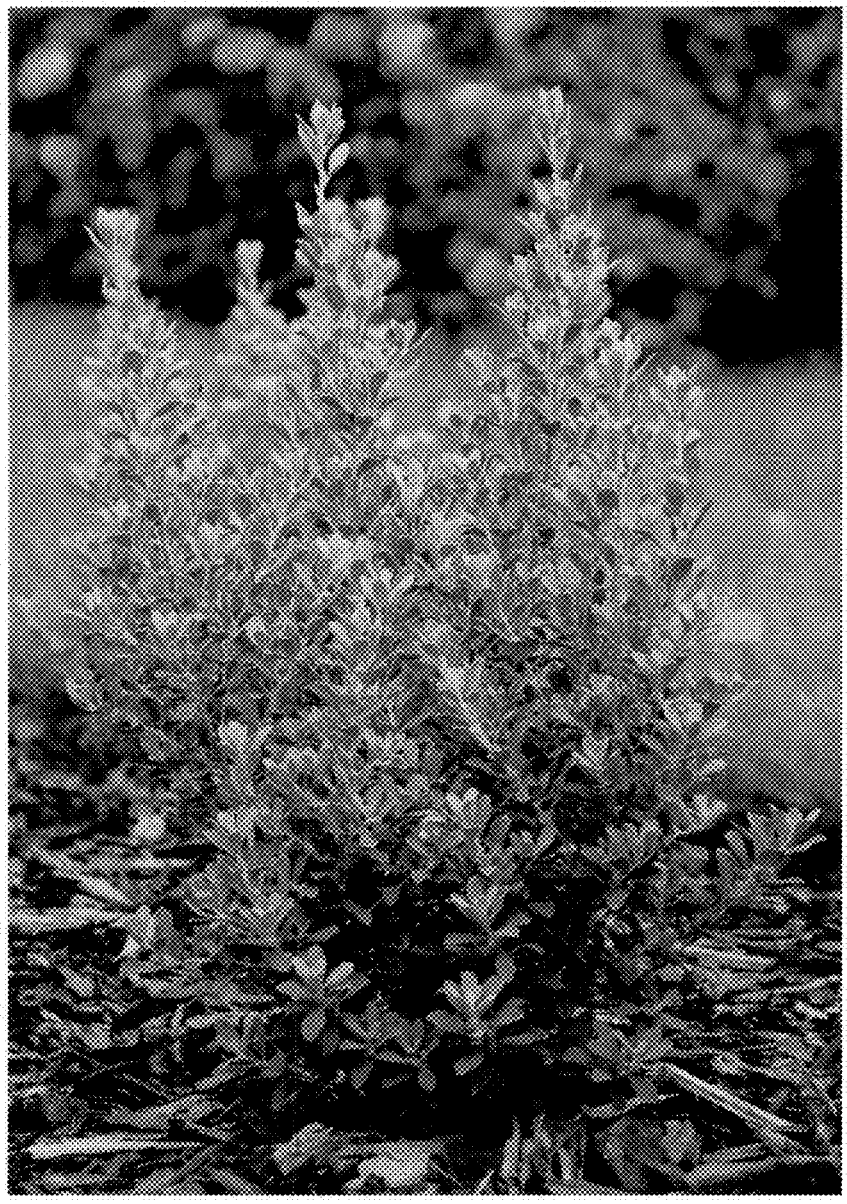

The accompanying photograph in FIG. 1 illustrates in full color a typical plant of 'JBN SC2' grown outdoors in Terrell, TX. This plant is approximately 2 years old, grown in the ground.

Figure 2:
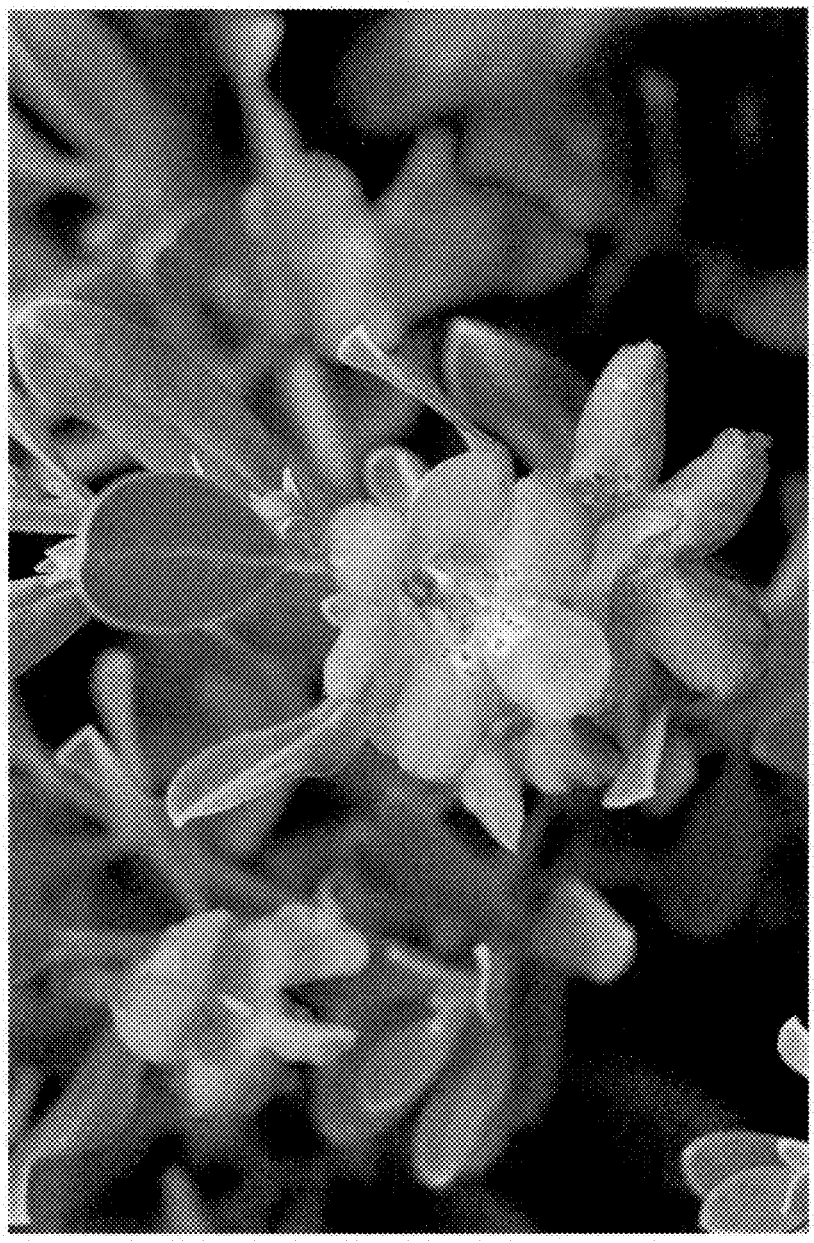

FIG. 2 illustrates in full color a close-up of a flower of 'JBN SC2'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'JBN SC2' plants grown in a poly-greenhouse in Grand Haven, Michigan. The plants were 3 years old.

Temperatures ranged from 15° C. to 21° C. at night to 18° C. to 27° C. during the day. No artificial light, photoperiodic treatments were given to the plants. Measurements and numerical values represent averages of typical plant types.

Botanical classification: *Leucophyllum frutescens* 'JBN SC2'.

PROPAGATION

Typical method: Softwood cuttings.
Root initiation: About 4 weeks in summer.
Time to produce rooted cutting: 10 to 12 weeks in summer.
Roots: Medium thickness, freely branching, fibrous, dense. Off-white in color, not accurately measured with R.H.S. chart.

PLANT

Plant type: Perennial shrub.
Growth habit: Compact.
Shape: Elliptic.
Height: 60 cm.
Plant spread: 65 cm.
Pot size of plant described: 3 gallon.
Age of plant described: Approximately 3 years.
Growth rate: Moderate.
Plant vigor: High.
Branching characteristics:
- *Habit*.—Basal, some pinching required to encourage a well-branched habit.
- *Number of lateral branches*.—About 12.
- *Shape*.—Rounded.
- *Color*.—New growth: RHS Yellow-Green 155A with Greyed-Green 193A pubescence. Mature growth: RHS Yellow-Green 155A with Greyed-Green 193A pubescence. Old growth: Near RHS Greyed-Green 197C.
- *Length*.—55 cm.
- *Width*.—5 mm.
- *Aspect*.—0° to 30° from vertical.
- *Strength*.—Moderate to high.
- *Pubescence*.—Yes.
- *Internode length*.—7 mm.

FOLIAGE

Leaf:
- *Arrangement*.—Alternate, single.
- *Shape*.—Obovate.
- *Length*.—2.25 cm.
- *Width*.—1 cm.
- *Apex*.—Obtuse.
- *Base*.—Attenuate.
- *Margin*.—Entire.
- *Texture of top surface*.—Soft and velvety; canescent.
- *Texture of bottom surface*.—Soft and velvety; canescent.
- *Pubescence*.—Yes, both sides.
- *Color*.—Young Foliage, Upper Side: RHS Green 138A. Young Foliage, Under Side: RHS Greyed-Green 194B. Mature Foliage, Upper Side: RHS Yellow-Green 147B. Mature Foliage, Under Side: Near RHS Greyed-Green 194B.

Venation:
- *Type*.—Pinnate.
- *Color*.—Upper Side: Venation is not distinct from leaf color. Under Side: RHS Greyed-Green 193A.

Petiole:
- *Length*.—2 mm.
- *Width*.—1 mm.
- *Color*.—Upper Side: RHS Yellow-Green 147B. Under Side: Near RHS Greyed-Green 194B.
- *Texture*.—Upper Side: Soft and velvety; canescent. Under Side: Soft and velvety; canescent.

FLOWER

Natural flowering season: Periodically flowering from late spring to first fall frost.
Flower type: Single.
Arrangement: Single flowers emerging from leaf axils along the lengths of lateral branches, particularly the terminal/upper half.
Quantity of flowers per lateral stem: About 10.
Quantity of buds per lateral stem: About 5.
Quantity of flowers and buds per plant: Several hundred.
Longevity on plant: Approximately 1 week.
Persistence: Self-cleaning.
Fragrance: Slightly peppery, mildly sweet fragrance; low intensity.

Bud:
- *Length*.—4 mm.
- *Diameter*.—3 mm.
- *Shape*.—Obovate.
- *Color*.—RHS Greyed-Purple 186C.

Flower:
- *Shape*.—Open funnel form.
- *Aspect*.—Outward.
- *Length*.—2 cm.
- *Width*.—2 cm.
- *Depth*.—2 cm.
- *Throat diameter*.—1 cm.
- *Tube length*.—1 cm.
- *Tube diameter*.—5 mm.

Petals:
- *Number*.—About 5 to 6.
- *Arrangement*.—Cruciform.
- *Shape*.—Globose.
- *Tip*.—Rounded.
- *Base*.—Fused.
- *Margin*.—Entire.
- *Length*.—1 cm.
- *Width*.—1 cm.
- *Texture*.—Upper side: Soft and silky; slightly pubescent. Under side: Soft and silky; glabrous.
- *Throat texture*.—Soft and silky; lightly pubescent with long, white hairs (pilose).
- *Tube texture*.—Soft and silky; glabrous.
- *Color*.—When Opening, Upper Side: RHS Purple N78B. When Opening, Under Side: RHS Purple N78C. Fully Opened, Upper Side: RHS Purple N78B. Fully Opened, Under Side: RHS Purple N78C. Tube, Outer Side: RHS Purple N78C. Tube, Inner Side: RHS Purple N78C with RHS White NN155B with Greyed-Yellow 162C speckles. Throat, Upper Side: RHS Purple N78C with RHS White NN155B with Greyed-Orange 175B speckles. Speckles are circular and approximately 0.5 mm in diameter; arranged roughly in 4 to 6 longitudinal rows along the length of lower half of throat. Approximately 30 to 50 in number.

Sepals:
*Number.*—4.
*Appearance.*—Relatively inconspicuous; narrow.
*Arrangement.*—Whorl.
*Shape.*—Narrowly elliptic.
*Tip.*—Acute.
*Base.*—Fused.
*Margin.*—Entire.
*Length.*—4 mm.
*Width.*—2 mm.
*Texture.*—Upper side: Pubescent. Under side: Pubescent.
*Color.*—Fully Opened, Upper Side: RHS Yellow-Green 147B. Fully Opened, Under Side: RHS Greyed-Green 194B.

Calyx:
*Shape.*—Collar-like.
*Length.*—5 mm.
*Width.*—7 mm.

Peduncle:
*Length.*—4 mm.
*Diameter.*—1 mm.
*Angle.*—45° relative to lateral branch.
*Strength.*—Moderate.
*Texture.*—Pubescent.
*Color.*—RHS Yellow-Green 147B.

REPRODUCTIVE ORGANS

Stamens:
*Number.*—4.
*Filament length.*—6 mm.
*Filament color.*—RHS White NN155A.

Anthers:
*Shape.*—Linear.
*Length.*—2 mm.
*Color.*—RHS Yellow-White 158A.
*Pollen amount.*—Sparse.
*Pollen color.*—RHS Yellow-White 158A.

Pistil:
*Number.*—1.
*Length.*—1.5 cm.

Stigma:
*Shape.*—Hemispherical.
*Color.*—RHS Purple N78C.
*Style length.*—1.4 cm.
*Style color.*—RHS Purple N78C.
*Ovary color.*—RHS Yellow-Green 145C.

OTHER CHARACTERISTICS

Fruit and seed: Not observed.

Disease resistance: Neither resistance nor susceptibility to the normal diseases and pests of *Leucophyllum* has been observed.

Drought tolerance and cold tolerance: Tolerant to USDA Zones 7(6b)-10.

What is claimed is:

1. A new and distinct cultivar of *Leucophyllum* plant named 'JBN SC2' as herein illustrated and described.

* * * * *